United States Patent [19]

Hawks

[11] Patent Number: 5,351,674

[45] Date of Patent: Oct. 4, 1994

[54] INLET TUBE FOR A SPECULUM

[76] Inventor: Robert A. Hawks, 17215 Lime Rock Dr., Sun City, Ariz. 85373

[21] Appl. No.: 979,179

[22] Filed: Nov. 20, 1992

Related U.S. Application Data

[63] Continuation-in-part of Ser. No. 850,469, Mar. 11, 1992.

[51] Int. Cl.$^5$ .............................................. A61B 1/00
[52] U.S. Cl. ................................. 128/3; 604/275; 604/41; 285/12
[58] Field of Search ............... 128/3, 4; 604/41, 275, 604/276; 285/12, 259, 238

[56] References Cited

U.S. PATENT DOCUMENTS

| | | | |
|---|---|---|---|
| 1,710,701 | 4/1929 | Hertzberg | 604/41 |
| 2,771,072 | 11/1956 | Montauge | 604/41 |
| 4,257,629 | 3/1981 | Maple et al. | 285/12 |
| 4,325,370 | 4/1982 | Young | 604/275 X |
| 4,459,318 | 7/1984 | Hyans | 604/275 X |
| 4,842,580 | 6/1989 | Ouelette | 604/275 X |
| 4,874,363 | 10/1989 | Abell | 604/276 X |
| 4,943,285 | 7/1990 | Hawks | 604/275 |

Primary Examiner—Richard J. Apley
Assistant Examiner—Karen A. Jalbert
Attorney, Agent, or Firm—Cahill, Sutton & Thomas

[57] ABSTRACT

A rectal speculum for use in conjunction with a colon lavage apparatus has a pair of opposed lateral inlets disposed at the distal end for receiving fecal matter. An inlet tube includes a first annular barb at the terminal end for engagement by the end of a first length of tubing and a second annular barb for engagement by the end of a second length of tubing after severance of the first annular barb.

2 Claims, 2 Drawing Sheets

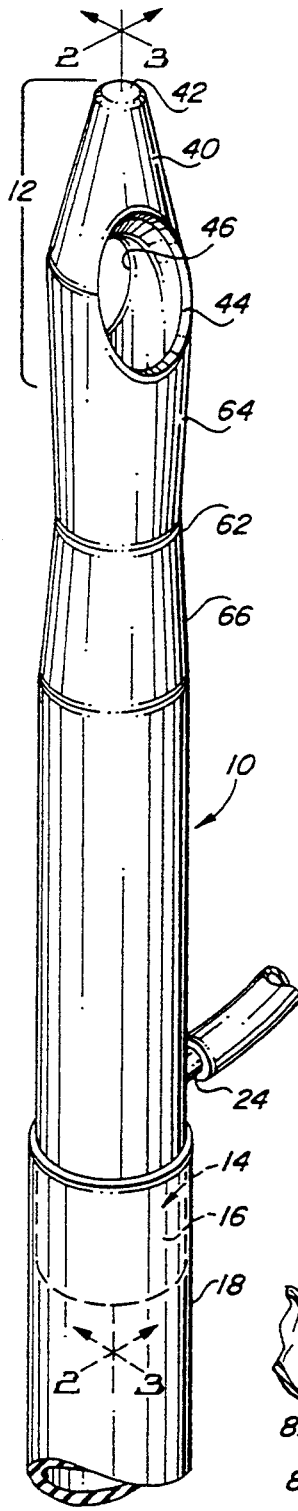
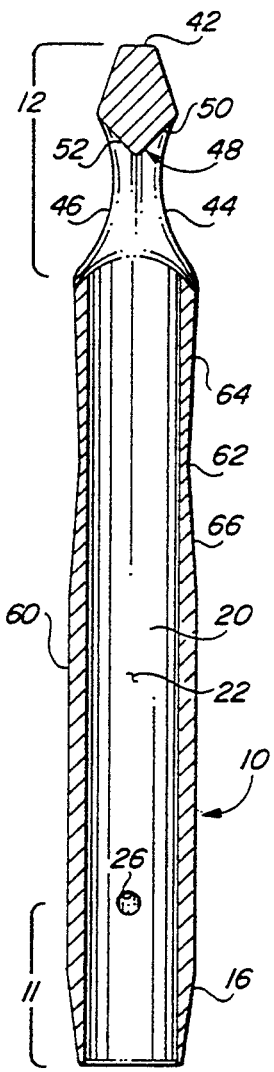
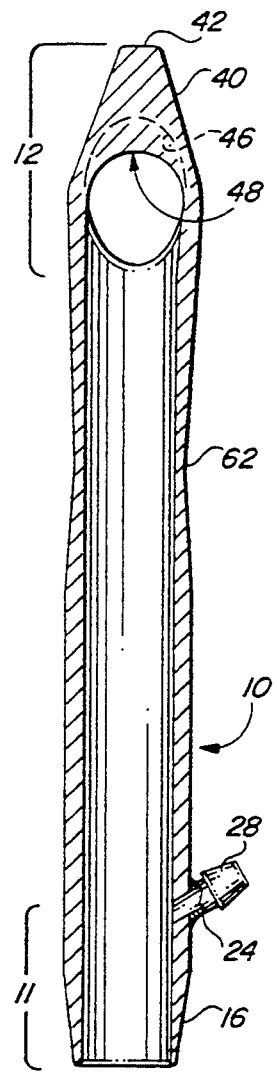
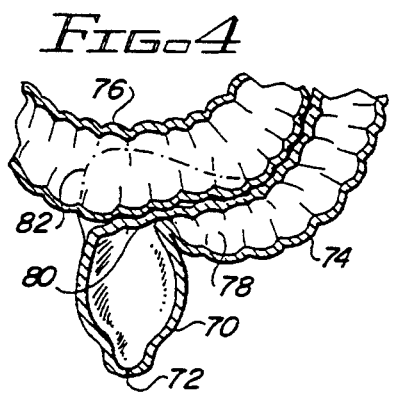
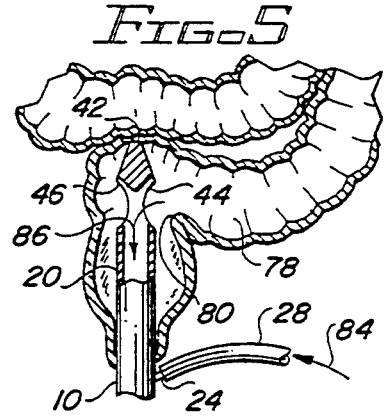

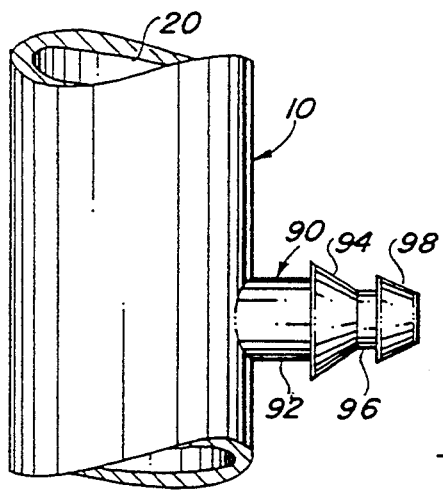
FIG.-6
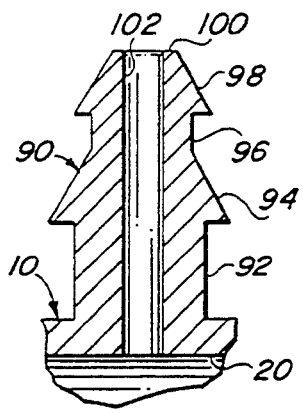
FIG.-7A
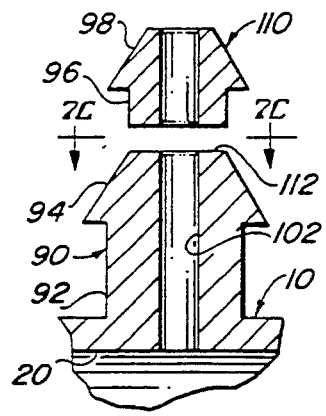
FIG.-7B
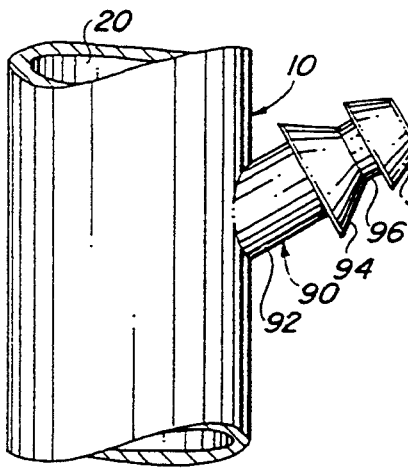
FIG.-8A
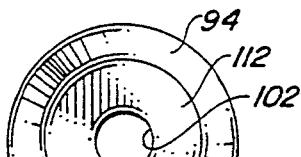
FIG.-7C
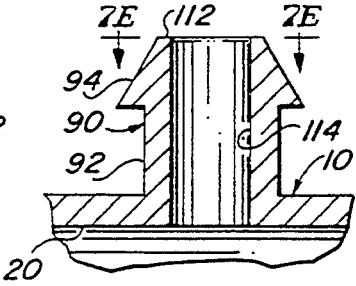
FIG.-7D
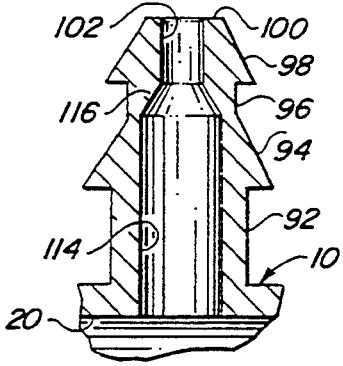
FIG.-7E
FIG.-8B
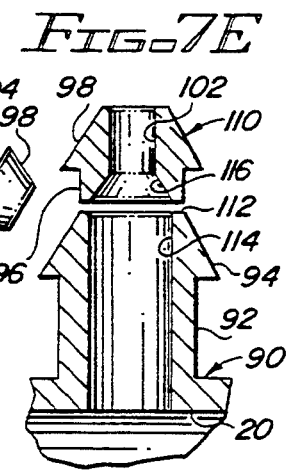
FIG.-9B
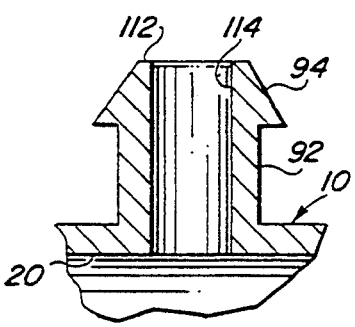
FIG.-9A
FIG.-9C

INLET TUBE FOR A SPECULUM

REFERENCE TO RELATED PATENTS

This application is a continuation in part of a copending application entitled "Speculum With Lateral Inlets", filed Mar. 11, 1992, assigned Ser. No. 07/850,469 and describing an invention by the present inventor.

This invention is also related to inventions by the present inventor described in U.S. Pat. Nos. 4,712,536 and 4,943,285.

BACKGROUND OF THE INVENTION

1. Field of the Invention

This invention relates to rectal specula and, more particularly, to a speculum for use with colon lavage apparatus.

2. Description of Related Art

Devices are known for lavaging the lower intestinal tract of patients suffering from colitis and similar ailments. These devices commonly employ a speculum for directing water or a treating fluid into the patient's colon and subsequently allowing the discharge of fluidized waste matter. One type of rectal speculum used with a colon lavage apparatus is formed of a pair of concentric tubes; an inlet tube carries the water into the patient's rectum and colon and a discharge tube allows fluidized waste matter to flow out.

Another type of speculum has a main tube-like body. In order to facilitate insertion of such a speculum into the patient's rectal canal, to decrease the patient's discomfort and possible pain and to avoid possible injury to the patient's intestinal tract, the speculum is usually used in conjunction with an obturator. A typical obturator is an elongated rod having a tapered cone-like portion at one end and a handle portion at the opposite end. The cone-like portion of the obturator is inserted through the hollow interior of the speculum from the proximal end to extend from the distal end. The cone-like portion closes the open end of the speculum and facilitates insertion of the speculum, minimizes discomfort and the likelihood of injury is reduced. Once a speculum is in place, the obturator is removed by gripping the handle portion and withdrawing the obturator from the speculum. Thereafter, a waste matter discharge conduit is attached to the distal end of the speculum.

Conventional specula suffer from a number of drawbacks. In particular, a speculum having a concentric tube structure is difficult and expensive to manufacture and it is inconvenient to clean and maintain. Generally, it is too expensive to manufacture and discard as a single use device. Furthermore, the process of attaching a discharge hose or conduit to the distal end of the tube type speculum after removal of the obturator creates discomfort and can be painful since the proximal end of the speculum is free to rock or slide in the patient's rectum during attachment.

In an effort to solve the first drawback of concentric tubes, the speculum described and illustrated in U.S. Pat. No. 4,712,536 includes an unobstructed main tube having a distal end for insertion into a patient's rectum and a proximal end connectable to a conduit. An inlet tube extends laterally from the main tube to introduce water or a cleansing fluid into the speculum and the patient's colon. To assist in attaching the conduit, a thumb rest is provided to facilitate stabilizing the speculum during such attachment.

U.S. Pat. No. 4,943,285 describes and illustrates an improved single tube speculum having an undulating surface for gripping engagement by the patient's rectal sphincter muscle during use of the speculum. Additionally, a water or treating fluid inlet is set at an angle with respect to the speculum to direct the fluid toward the proximal end of the speculum.

Both of the specula described above define an inlet opening at the distal end. To ease insertion, an obturator is employed which projects a cone-like element from the inlet and which serves as a guide to ease penetration and expansion of the anus and colon to receive the speculum. The obturator includes a handle disposed at the proximal end of the speculum. This handle is gripped to withdraw the obturator from the speculum after insertion. Because of the requirement for removal of the obturator through the proximal end, the conduit for the waste matter must be attached after insertion of the speculum. The process of attaching the conduit to the speculum may be painful and usually incurs discomfort.

SUMMARY OF THE INVENTION

A speculum has a cone-like distal end to facilitate penetration through the anus and into the colon to lodge the speculum in place. A pair of opposed laterally open inlets are located proximate to the distal end to permit inflow of fecal matter even under conditions of prolapse of the large intestine. An annular depression proximate of the opposed inlets is gripped by the rectal sphincter muscle to assist in retaining the speculum in place during use. A conduit for conveying fluidized fecal matter may be attached to the proximal end of the speculum prior to insertion to avoid the discomfort of attaching the conduit after insertion. A lateral inlet tube accommodates introduction of water or treating fluid to assist in fluidizing and in outflow of the fecal matter. The lateral inlet tube may be perpendicular to the longitudinal axis of the speculum, angled toward the distal end of the speculum or angled toward the proximal end of the speculum. The inlet tube includes a nipple having an annular barb for receiving ¼ inch tubing. The nipple may be severed to render accessible a larger diameter annular barb to accommodate ⅜ inch tubing. Upon severance of the nipple, the diameter of the passageway in the remaining inlet tube may be enlarged to accommodate the increased flow rate of the ⅜ inch tubing or this part of the inlet tube may be formed with an enlarged passageway.

It is therefore a primary object of the present invention to provide a speculum for receiving fecal matter under conditions of prolapse of the large intestine.

Another object of the present invention is to provide a speculum which permits attachment of different diameter tubing to a water inlet tube.

Yet another object of the present invention is to provide a speculum having a water inlet tube adaptable for attachment with different diameter water introducing tubing.

Still another object of the present invention is to provide a speculum having a water inlet tube angled toward or away from a pair of opposed inlets to assist in fluidizing any fecal matter prior to entry into the pair of inlets.

A further object of the present invention is to provide a speculum having a pair of laterally oriented opposed inlets for receiving fecal matter and a water inlet tube to assist in discharging fluidized fecal matter.

A yet further object of the present invention is to provide a speculum which enhances self treatment of colon lavage.

A still further object of the present invention is to provide a throwaway one piece one time use speculum usable with colon lavage apparatus.

These and other objects of the present invention will become apparent to those skilled in the art as the description thereof proceeds.

BRIEF DESCRIPTION OF THE DRAWINGS

The present invention will be described with greater specificity and clarity with reference to the following drawings, in which:

FIG. 1 is a perspective view of a speculum;

FIG. 2 is a cross-sectional view taken along lines 2—2, shown in FIG. 1;

FIG. 3 is a cross-sectional view taken along lines 3—3, as shown in FIG. 1;

FIG. 4 is a partial cross-sectional view illustrating prolapse of the large intestine;

FIG. 5 illustrates use of the speculum with prolapsus;

FIG. 6 illustrates a water inlet tube angled perpendicularly to the speculum;

FIG. 7a is a cross-sectional view of the inlet tube;

FIG. 7b illustrates detachment of a nipple from the inlet tube;

FIG. 7c is a top view taken along lines 7c—7c, as shown in FIG. 7b;

FIG. 7d is a cross-sectional view of the enlarged passageway within the inlet tube;

FIG. 7e is a top view taken along lines 7e—7e, as shown in FIG. 7d;

FIG. 8a illustrates the inlet tube angled toward the distal end of the speculum;

FIG. 8b illustrates the inlet tube angled toward the proximal end of the speculum;

FIG. 9a illustrates a cross-sectional view of a variant of the inlet tube;

FIG. 9b illustrates a severed nipple of the inlet tube variant; and

FIG. 9c illustrates the enlarged passageway in the inlet tube variant.

DESCRIPTION OF THE PREFERRED EMBODIMENT

Referring jointly to FIGS. 1, 2 and 3, there is illustrated a speculum 10 having a distal end 12 and a proximal end 14. The proximal end may include a tapered section 16 for receiving and supporting a conduit 18, which conduit conveys fluidized fecal or waste matter from the speculum. Speculum 10 includes a passageway 20 defined by an interior cylindrical surface 22. An inlet tube 24 is in fluid communication with passageway 20 through aperture 26 in cylindrical surface 22. A length of tubing 28 interconnects inlet tube 24 with a source of water or treatment fluid to provide a flow of fluid into passageway 20. As particularly illustrated in FIG. 3, inlet tube 24 is angled to inject a stream of the fluid toward proximal end 14 of speculum 10.

Distal end 12 includes a tapered end 40, which end may be of a constant taper (arithmetically tapered), as shown, or it may be geometrically tapered. Tip 42 is preferably blunted to minimize the possibility of painful or injurious penetration of the walls of the colon or large intestine during insertion or use of the speculum.

A pair of opposed laterally oriented inlets 44,46 in fluid communication with passageway 20 are formed in distal end 12. A posteriorly tapered wall 48 is disposed intermediate the distal portions of inlets 44,46 and includes opposed canted surfaces 50,52 to direct fluidized fecal matter posteriorly into passageway 20. Preferably, the junction between inlets 44 and 46 with passageway 20 is smooth surfaced to eliminate restriction and enhance flow into the passageway.

Exterior 60 of speculum 10 includes an annular depression 62 located posteriorly of inlets 44,46. This depression may be developed by posteriorly tapering cone-like surface 64 and anteriorly tapering cone-like surface 66. Surfaces 64 and 66 may be arithmetically or geometrically tapered.

Referring to FIG. 4, there is illustrated a typical colon 70 terminated by anus 72. The colon is located at the terminal end of large intestine 74. A medical condition known as prolapsus usually occurs as a result of disease, health problems or simply age. This condition is characterized by translation of a normally horizontally oriented segment of the large intestine to a downward location essentially resting upon colon 70, as illustrated in FIG. 4 and depicted by intestine section 76. This condition tends to force wall 78 at the terminal end of the large intestine against the upper end of the colon and sometimes closes entrance 80 to the colon, as illustrated. Under normal conditions, wall 78 at the terminal end of large intestine 74 would extend upwardly from the colon, as depicted by dashed line 82.

Conventional and previously known specula for colon lavage include an axially oriented inlet at the distal tip. Upon insertion of a speculum of this type under conditions of prolapse of the large intestine, as depicted in FIG. 4, the inlet to the speculum would be restricted, if not blocked, by intestine wall 78 at entrance 80 of colon 70. Such blockage or restriction of the inlet to the speculum would severely impede inflow of fecal matter. Thus, the effectiveness of the colon lavage would be compromised. Furthermore, great discomfort to the patient would occur and a real possibility for injury to the delicate tissues would be present. The speculum illustrated in FIGS. 1, 2 and 3 is admirably suited to accommodate a prolapsed large intestine with little, if any, discomfort and minimal likelihood of injury.

FIG. 5 illustrates use of speculum 10 in a condition of prolapsus, as depicted in FIG. 4. Speculum 10 is inserted through anus 72 and colon 70 in the normal manner. Upon contact by tip 42 with intestine wall 78, the blunt shape of the tip will urge the wall upwardly to open entrance 80 of the colon to penetration by the speculum. It may be noted that because the inlet to the speculum is not at the tip of the distal end, even draping of intestine wall 78 about the tip will not affect flow of fecal matter into the speculum.

Inlet 44 is shown as facing the flow of fecal matter disposed within the terminal end of the large intestine. Such orientation will enhance entry of the fecal matter into the speculum. Because inlets 44 and 46 are opposed, reorientation of speculum 10 ninety degrees about its longitudinal axis will present at least half of each of inlets 44 and 46 to inflow of fecal matter. Thus, under any orientation of the speculum about its longitudinal axis, a substantial entryway area through one or both of the inlets will exist. Such substantial entryway area, in combination with the forced displacement of intestine wall 78 will enhance inflow.

As particularly illustrated in FIG. 5, water or treatment fluid is injected, as depicted by arrow 84, through tubing 28 and inlet tube 24 into passageway 20 within speculum 10. By closing conduit 18 (see FIG. 1), such water or treatment fluid will be forced upwardly through passageway 20 and be ejected through outlets 44,46 with the resulting effect of fluidizing the fecal matter to enhance evacuation through the speculum. The orientation of inlet tube 24 toward proximal end 14 of the speculum will enhance and encourage flow of fecal matter from the speculum into conduit 18, as depicted by arrow 86. Depending upon the state of liquification of the fecal matter within the large intestine, several cycles of forcing the water or treatment fluid into the large intestine may be necessary to obtain evacuation to the degree desired.

All previously known specula require the attachment of a conduit for conveying the fecal matter to be attached subsequent to insertion. The mechanical manipulation of such attachment renders self administration of colon lavage very difficult to manipulate. Accordingly, assistance is required. Because speculum 10 permits attachment of the conduit 18 prior to insertion and use, speculum 10 may be readily used for self administered colon lavage. Furthermore, the discomfort and opportunity for injury during attachment of the conduit to an inserted speculum are completely avoided.

Referring to FIG. 6, there is shown a segment of speculum 10 and a variant inlet tube 90. In this embodiment, the inlet tube is illustrated as being essentially perpendicular to the longitudinal axis of speculum 10. Referring jointly to FIG. 6, 7a, 7b, 7c and 7d the structure and configuration of variant inlet tube 90 will be described. As depicted by the cross-section views, the variant inlet tube may be formed with and as a part of speculum 10. Alternatively, it may be a separate element lodged within a correspondingly sized aperture in the wall of the speculum. The form of attachment may be by welding, adhesives, etc. The variant inlet tube includes a cylindrical section 92 extending from the side wall of speculum 10. An annular barb 94 tops cylindrical section 92. This annular barb includes a conical surface diametrically expanding toward the speculum. A further cylindrical element extends from the upper end of annular barb 94. A further annular barb 98 tops cylindrical section 96. Upper end 100 of annular barb 98 is truncated, as illustrated. A central passageway 102 extends through annular barb 98, cylindrical section 96, annular barb 94 and cylindrical section 92 into fluid communication with passageway 20 within speculum 10.

The diametric size of annular barb 98 is configured to mate with standard ¼ inch diameter flexible plastic tubing useful in introducing water to variant inlet tube 90. Because of the barb, the tubing will be constrained from sliding off of the variant inlet tube during normal use. Water flow through the tubing will be conveyed through passageway 102 into passageway 20 to assist in fluidizing the fetal matter and permit discharge of liquified fecal matter through conduit 18 (see FIG. 1).

Certain colonic lavage apparatus includes fittings for ⅜ inch flexible tubing to convey water to a speculum. Such tubing is of a size too large to be firmly retained by annular barb 98. To accommodate such larger sized tubing, nipple 110 is cut off, as indicated in FIG. 7b. The nipple consists of annular barb 98 and cylindrical section 96. Top end 112 of variant inlet tube 90 is defined by the truncated surface of annular barb 94. Annular barb 94 is of a diameter commensurate with sliding engagement of ⅜ inch plastic tubing and causes sufficient expansion of the tubing upon engagement to prevent inadvertent disengagement during normal use. Because passageway 102 is diametrically configured to accommodate primarily ¼ inch plastic tubing, it is useful to diametrically expand the passageway to permit a greater flow rate of water flowing through the ⅜ inch diameter tubing without creating unnecessary restriction to water inflow.

After removal of nipple 110, passageway 102 extending through annular barb 94 and cylindrical section 92 is diametrically enlarged to form passageway 114, as illustrated in FIG. 7d. This larger passageway is commensurate with the passageway through the ⅜ inch diameter tubing and a greater flow rate is accommodated than that possible through passageway 102 without creating an increased velocity that may be detrimental.

Removal of nipple 110 may be accomplished with a pair of nippers, a knife or other cutting implement. Enlargement of passageway 102 to passageway 114 may be accommodated by drilling. As variant inlet tube 90 is of plastic material in a disposal configuration of speculum 10, drilling out of the passageway is readily accomplished with low or high speed drill bits rotated by manual or electrically operated drills.

Referring to FIG. 8a, there is illustrated variant inlet tube 90 angled toward the distal end of speculum 10. With such angular attachment, water flow through the variant inlet tube will be oriented toward the proximal end of the speculum to assist in discharging liquified fecal matter through the speculum. As discussed previously, water flow through the opposed inlets at the distal end of the speculum can readily be urged by crimping conduit 18.

Referring to FIG. 8b, variant inlet tube 90 is shown angled toward the proximal end of speculum 10. With such orientation, the water flowing through the variant inlet tube into passageway 20 will be urged toward the distal end of the speculum to assist in introducing water into the large intestine through the inlets at the distal end of the speculum. This orientation is therefore useful in assisting or urging liquification of any fecal matter prior to entry into the speculum and within the speculum.

Referring jointly to FIGS. 9a, 9b and 9c, there is illustrated a modification of variant inlet tube 90 which eliminates the need to drill out passageway 102. In this configuration, passageway 102 extends only part way through the nipple defined by annular barb 96 and cylindrical section 98. Enlarged passageway 114 is disposed interior of annular barb 94 and cylindrical section 92 to accommodate flow from both ¼ inch tubing or ⅜ inch tubing attached to the variant inlet tube. At, or in the vicinity of, cylindrical section 96 there is disposed a transition passageway 116 which interconnects passageway 102 and passageway 114. This transition passageway may be in the form of a truncated cone, as illustrated. Alternatively, it may be in the nature of a shoulder extending transverse to the longitudinal axis of passageways 102, 114. Upon removal of nipple 10, as illustrated in FIG. 9b, passageway 102 and transitional passageway 116 will be removed to expose the full diameter of passageway 114 proximate end 112. The final configuration, as illustrated in FIG. 9c, will eliminate the need to drill out passageway 102.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles

I claim:

1. A speculum for use in a colonic lavage procedure, said speculum comprising in combination:
   a) a cylindrical surface defining a passageway extending through said speculum and having a tapered distal end and a proximal end for introducing a fluid and for discharging liquified fecal matter, respectively;
   b) a pair of inlets disposed at the tapered distal end of said passageway for introducing the fluid into the colon and for receiving the liquified fecal matter;
   c) a blunt closed tip disposed at the distal end and terminating the distal end to displace the wall portion of the colon on contact without producing trauma to the wall portion in the event of a prolapse condition;
   d) an inlet tube disposed toward the proximal end of said passageway for conveying the fluid from a source of fluid into said passageway, said inlet tube including a first annular barb of a first diameter for engagement by the end of a first length of tubing in fluid communication with the source of fluid, a second annular barb of a second diameter for alternative engagement by the end of a second length of tubing in fluid communication with the source of fluid, said first annular barb being severable from said inlet tube; and
   e) a bore extending through said inlet tube, said bore being of a first diameter proximate said first barb and of a second and greater diameter proximate said second barb, said second barb being of a greater diameter than said first barb.

2. A speculum having a tapered distal end and a proximal end for use in a colonic lavage procedure to fluidize and to extract fecal matter, said speculum comprising in combination:
   a) an uninterrupted cylindrical surface defining a passageway extending through said speculum for introducing a fluid into the colon and for discharging liquified fecal matter;
   b) a pair of opposed inlets disposed in the distal end of said speculum for discharging fluid from said passageway into the colon and for receiving liquified fecal matter into said passageway;
   c) a blunt closed tip terminating the distal end for displacing a wall portion of the colon on contact without producing trauma to the wall portion in the event of a prolapse condition;
   d) an inlet tube disposed toward the proximal end of said speculum for introducing fluid into said passageway from a source of fluid, said inlet tube including a first annular barb for securing an end of a first length of tubing in fluid communication with the source of fluid and a second annular barb of a greater diameter than said first annular barb for securing an end of a second length of tubing having a diameter larger than the first length of tubing; and
   e) a first bore disposed within said inlet tube coincident with at least said first annular barb and a second bore of a larger diameter than said first bore within said inlet tube coincident with at least said second annular barb.

* * * * *